(12) United States Patent
Penzel et al.

(10) Patent No.: US 8,829,232 B2
(45) Date of Patent: Sep. 9, 2014

(54) PROCESS FOR PREPARING AROMATIC ISOCYANATES

(75) Inventors: Ulrich Penzel, Tettau (DE); Torsten Mattke, Freinsheim (DE); Andreas Wölfert, Bad Rappenau (DE); Johannes Jacobs, Ossendrecht (NL); Tsung-Chieh Cheng, Heppenheim (DE); Kerstin Heinen, Lorsch (DE); Eckhard Stroefer, Mannheim (DE); Stefan Maixner, Schwetzingen (DE); Wolfgang Mackenroth, Bad Dürkheim (BE); Christian Tragut, Sterrebeck (BE); Kai Thiele, Antwerp (BE); Myung Un Won, Soho dong Yeosu (KR)

(73) Assignee: BASF SE, Ludwigshafen (DE)

( * ) Notice: Subject to any disclaimer, the term of this patent is extended or adjusted under 35 U.S.C. 154(b) by 759 days.

(21) Appl. No.: 13/057,869

(22) PCT Filed: Aug. 6, 2009

(86) PCT No.: PCT/EP2009/060184
§ 371 (c)(1),
(2), (4) Date: Jul. 5, 2011

(87) PCT Pub. No.: WO2010/015667
PCT Pub. Date: Feb. 11, 2010

(65) Prior Publication Data
US 2011/0251425 A1 Oct. 13, 2011

(30) Foreign Application Priority Data
Aug. 7, 2008 (EP) ...................................... 08161976

(51) Int. Cl.
*C07C 263/00* (2006.01)
*C07C 263/10* (2006.01)
(52) U.S. Cl.
CPC .................................. *C07C 263/10* (2013.01)
USPC ......................................................... 560/347
(58) Field of Classification Search
None
See application file for complete search history.

(56) References Cited

U.S. PATENT DOCUMENTS

| 2005/0113601 A1 | 5/2005 | Herold et al. |
| 2007/0043233 A1 | 2/2007 | Sanders et al. |
| 2008/0027242 A1 | 1/2008 | Knosche et al. |

FOREIGN PATENT DOCUMENTS

| DE | 300 168 | 5/1992 |
| DE | 300168 A7 * | 5/1992 |

OTHER PUBLICATIONS

U.S. Appl. No. 13/266,049, filed Oct. 24, 2011, Stroefer, et al.
U.S. Appl. No. 13/163,928, filed Jun. 20, 2011, Rosendahl, et al.
U.S. Appl. No. 13/109,399, filed May 17, 2011, Raichle, et al.
U.S. Appl. No. 13/394,647, filed Mar. 7, 2012, Mattke, et al.
U.S. Appl. No. 13/380,357, filed Dec. 22, 2011, Schelling, et al.
U.S. Appl. No. 13/380,680, filed Dec. 23, 2011, Schelling, et al.
U.S. Appl. No. 13/383,549, filed Jan. 11, 2012, Schelling, et al.
U.S. Appl. No. 13/383,433, filed Jan. 11, 2012, Schelling, et al.
International Search Report Issued Jan. 18, 2010 in PCT/EP09/060184 filed Aug. 6, 2009.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

The invention relates to a process for preparing isocyanates by reacting the corresponding amines with phosgene in the liquid phase, if appropriate in the presence of at least one inert medium, in which the amine and the phosgene are first mixed in a mixing chamber (1) to give a reaction mixture and the reaction mixture is fed to a reactor, the amine being added through an orifice (3) arranged coaxially to the mixing chamber (1) and the phosgene being added through feed orifices (5) in at least two planes (7, 9) arranged at right angles to the axis (11) of the mixing chamber (1), or the phosgene being added through the orifice (3) arranged coaxially to the mixing chamber and the amine through the feed orifices (5) in at least two planes (7, 9) arranged at right angles to the axis (11) of the mixing chamber (1). At least one plane (9) is arranged upstream and at least one plane (7) downstream of the orifice (3) arranged coaxially to the mixing chamber (1) in main flow direction of the reaction mixture. The mean residence time of the reaction mixture in the mixing chamber (1) is not more than 20 ms.

13 Claims, 1 Drawing Sheet

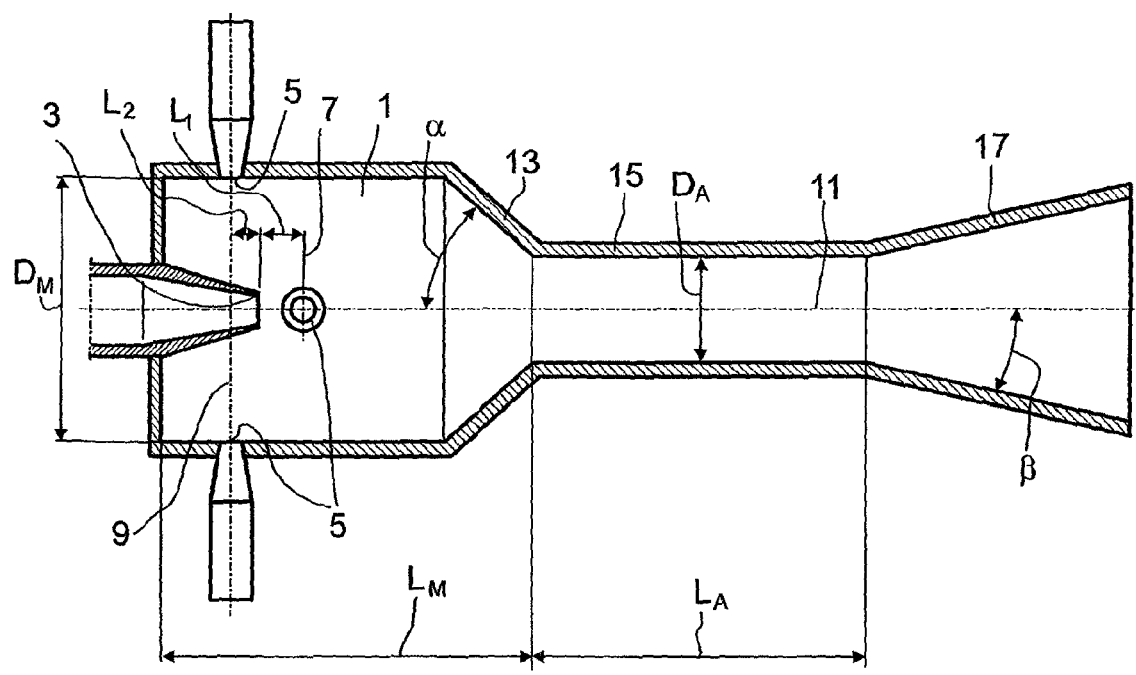

PROCESS FOR PREPARING AROMATIC ISOCYANATES

CROSS-REFERENCE TO RELATED APPLICATIONS

This application is a National Stage of PCT/EP2009/060184 filed on Aug. 6, 2009. This application is based upon and claims the benefit of priority to European Application No. 08161976.9 filed on Aug. 7, 2008.

BACKGROUND OF THE INVENTION

The invention relates to a process for preparing isocyanates by reacting the corresponding amines with phosgene in the liquid phase, if appropriate in the presence of at least one inert medium, in which the amine and the phosgene are first mixed in a mixing chamber to give a reaction mixture and the reaction mixture is fed to a reactor. The amine is added through an orifice arranged coaxially to the mixing chamber and the phosgene is added through feed orifices in at least two planes arranged at right angles to the axis of the mixing chamber. At least one plane is arranged upstream and one plane downstream of the orifice for addition of the amine in main flow direction of the reaction mixture.

Isocyanates can be prepared by phosgenating the corresponding amines, in principle by a liquid phase or gas phase phosgenation. Liquid phase phosgenation is notable in that the reaction can be carried out at lower temperatures than the gas phase phosgenation and no evaporation of the reactants is required.

In liquid phase phosgenation, an amine-containing reactant stream is fed in in the liquid phase. This is mixed with a phosgene-containing reactant stream. The phosgene may be dissolved in an inert solvent. Subsequently, the phosgene-containing reactant stream is sprayed into a mixing chamber in which it is mixed with the amine-containing reactant stream. The amine and the phosgene react with release of HCl to give the corresponding isocyanates.

Rapid mixing of the amine with the phosgene is necessary, since the isocyanate formed, in the case of too low a phosgene concentration, reacts with the excess amine to give urea or other troublesome, high-viscosity and solid by-products. For this reason, rapid mixing and a short residence time in the reaction chamber are required.

An apparatus in which the amine and the phosgene are first mixed in a mixing chamber to give a reaction mixture and the reaction mixture is then fed to a reactor, the amine being added through an orifice arranged coaxially to the mixing chamber and the phosgene being added through feed orifices in at least two planes arranged at right angles to the axis of the mixing chamber, is described, for example, in DD-A 300 168.

It is an object of the present invention to provide a process for preparing isocyanates by reacting the corresponding amines with phosgene in the liquid phase, in which a lower level of secondary component formation can be achieved compared with the processes known from the prior art.

BRIEF SUMMARY OF THE INVENTION

The object is achieved by a process for preparing isocyanates by reacting the corresponding amines with phosgene in the liquid phase, if appropriate in the presence of at least one inert medium, in which the amine and the phosgene are first mixed in a mixing chamber to give a reaction mixture and the reaction mixture is fed to a reactor. The amine is added through an orifice arranged coaxially to the mixing chamber and the phosgene is added through feed orifices in at least two planes arranged at right angles to the axis of the mixing chamber. At least one plane is arranged upstream and one plane downstream of the orifice for addition of the amine in main flow direction of the reaction mixture. According to the invention, the mean residence time of the reaction mixture in the mixing chamber is not more than 18.5 ms.

BRIEF DESCRIPTION OF THE FIGURE

FIG. 1 depicts a cross-sectional view of one embodiment of an apparatus of the present invention which is suitable for mixing amine and phosgene in a liquid phase.

DETAILED DESCRIPTION OF THE INVENTION

The short residence time of the reaction mixture in the mixing chamber of not more than 18.5 ms allows a reduced level of secondary component formation to be achieved compared to the processes known from the prior art.

The mean residence time in the mixing chamber is calculated from $$t_s = \frac{V}{V^*}.$$

In this formula, $t_s$ means the residence time, $V$ the volume of the mixing chamber and $V^*$ the total volume flow of the reactant streams. The volume of the mixing chamber is the volume up to the end of the constriction, i.e. up to the entry into the zone with constant cross section which follows the mixing chamber downstream. The volume of the central nozzle which projects into the mixing chamber is not part of the volume of the mixing chamber.

The amine used to prepare isocyanates is, for example, a monoamine, a diamine, a triamine or higher-functionality amine. However, preference is given to using monoamines or diamines. According to the amine used, the corresponding monoisocyanates, diisocyanates, triisocyanates or higher-functionality isocyanates are formed. Preference is given to preparing monoisocyanates or diisocyanates by the process according to the invention.

The amines and isocyanates may be aliphatic, cycloaliphatic or aromatic. Cycloaliphatic isocyanates are those which comprise at least one cycloaliphatic ring system.

Aliphatic isocyanates are those which have exclusively isocyanate groups bonded to straight or branched chains.

Aromatic isocyanates are those which have at least one isocyanate group bonded to at least one aromatic ring system.

In the context of this application, (cyclo)aliphatic isocyanates is a short form of cycloaliphatic and/or aliphatic isocyanates.

Examples of aromatic diisocyanates are monomeric diphenylmethane 2,4'- or 4,4'-diisocyanate (MDI) and higher oligomers thereof (PMDI) or mixtures thereof, toluene 2,4- and/or 2,6-diisocyanate (TDI) and naphthalene 1,5- or 1,8-diisocyanate (NDI).

Preferred (cyclo)aliphatic diisocyanates are those having from 4 to 20 carbon atoms.

Examples of customary aliphatic diisocyanates are tetramethylene 1,4-diisocyanate, hexamethylene diisocyanate (1,6-diisocyanatohexane), octamethylene 1,8-diisocyanate, decamethylene 1,10-diisocyanate, dodecamethylene 1,12-diisocyanate, tetradecamethylene 1,14-diisocyanate, derivatives of lysine diisocyanate, tetramethylxylylene diisocyanate (TMXDI), trimethylhexane diisocyanate or tetramethylhexane diisocyanate, and also 3(or 4),8(or 9)-bis(isocyanatomethyl)tricyclo[5.2.1.0$^{2.6}$]decane isomer mixtures, and cycloaliphatic diisocyanates such as 1,4-, 1,3- or 1,2-diisocyanatocyclohexane, 4,4'- or 2,4'-di(isocyanatocyclohexyl) methane, 1-isocyanato-3,3,5-trimethyl-5-(isocyanatomethyl)cyclohexane (isophorone diisocyanate), 1,3- or 1,4-bis (isocyanatomethyl)cyclohexane, 2,4- or 2,6-diisocyanato-1-methylcyclohexane.

Particular preference is given to MDI/PMDI isomer and oligomer mixtures, and to TDI isomer mixtures.

To prepare monoisocyanates, it is likewise possible to use aliphatic, cycloaliphatic or aromatic amines. A preferred aromatic amine is especially aniline.

The phosgene can be dissolved in an inert solvent before addition to the mixing chamber. Suitable inert solvents in which the phosgene is dissolved are, for example, chlorinated aromatic hydrocarbons, for example monochlorobenzene or dichlorobenzene, or else toluene. The ratio of phosgene to inert solvent is preferably in the range from 1:0 to 1:2, especially in the range from 1:0 to 1:1.

In a preferred embodiment, the phosgene is added via in each case at least two feed orifices in the at least two planes arranged at right angles to the axis of the mixing chamber. The feed orifices through which the phosgene is added are preferably arranged such that the main directions of the feed orifices meet in the axis of the mixing chamber. By virtue of the arrangement of the feed orifices such that the main directions meet in the axis of the mixing chamber, the phosgene jets added via the feed orifices directly meet the amine which is added through the orifice arranged coaxially to the mixing chamber. This achieves rapid mixing of phosgene and amine. In particular, phosgene jets which leave the feed orifices also meet at the axis of the mixing chamber. This gives rise to a homogeneous phosgene distribution in flow direction of the amine.

It is also preferred when the feed orifices of the first plane are arranged rotated about the axis of the mixing chamber with respect to the feed orifices of the second plane. It is particularly preferred when the feed orifices, in the case of two feed orifices each per plane, are arranged rotated by 90 degrees with respect to one another.

The mixing chamber in which the amine is mixed with the phosgene preferably has a ratio of length to diameter (L/D ratio) which is in the range from 1 to 2 and especially in the range from 1 to 1.5. The orifice arranged coaxially to the axis of the mixing chamber, through which the amine is added, preferably projects into the mixing chamber. To this end, the orifice through which the amine is added is configured, for example, as a nozzle. The orifice through which the amine is added is then the exit orifice of the nozzle. The ratio of the diameter of the orifice through which the amine is added based on the diameter of the mixing chamber is preferably in the range from 0.05 to 0.5, more preferably in the range from 0.1 to 0.4 and especially in the range from 0.15 to 0.35.

When the phosgene is added through feed orifices in two planes arranged at right angles to the axis of the mixing chamber, one plane being arranged upstream and one plane downstream of the orifice for addition of the amine in main flow direction of the reaction mixture, the ratio of the distance of the plane which is arranged downstream of the orifice through which the amine is added from the orifice through which the amine is added, based on the diameter of the mixing chamber, is in the range from 0 to 1, more preferably in the range from 0.01 to 0.5 and especially in the range from 0.05 to 0.2. When the phosgene is added through feed orifices in more than one plane arranged at right angles to the axis of the mixing chamber, said planes being arranged downstream of the orifice through which the amine is added in main flow direction of the reaction mixture, the distance of the feed orifices of the plane which is closest to the orifice through which the amine is added corresponds to the distance of the plane of the feed orifices when only one plane is arranged downstream of the orifice through which the amine is added.

When the phosgene is added through feed orifices in two planes arranged at right angles to the axis of the mixing chamber, one plane being arranged upstream and one plane downstream of the orifice for addition of the amine in main flow direction of the reaction mixture, the ratio of the distance of the plane which is arranged upstream of the orifice through which the amine is added from the orifice through which the amine is added, based on the diameter of the mixing chamber, is in the range from 0 to 1, more preferably in the range from 0.01 to 0.5 and especially in the range from 0.05 to 0.2. When the phosgene is added through feed orifices in more than one plane arranged at right angles to the axis of the mixing chamber, said planes being arranged upstream of the orifice through which the amine is added in main flow direction of the reaction mixture, the distance of the feed orifices of the plane which is closest to the orifice through which the amine is added corresponds to the distance of the plane of the feed orifices when only one plane is arranged upstream of the orifice through which the amine is added.

The phosgene is preferably added through feed orifices in a maximum of five planes arranged at right angles to the axis of the mixing chamber. It is more preferred when the phosgene is added through feed orifices in a maximum of three planes arranged at right angles to the axis of the mixing chamber, and particularly preferred when the phosgene is added through feed orifices in two planes arranged at right angles to the axis of the mixing chamber.

The number of feed orifices in the individual planes is preferably not more than five, more preferably not more than four and especially two. The number of feed orifices in the individual planes gives rise to a good distribution of the phosgene in the mixing chamber. In this context, it is additionally preferred when the orifices of the individual planes are rotated with respect to one another, such that the feed orifices of the individual planes are not aligned in flow direction. In the case of feed orifices in more than two planes, the feed orifices of the individual planes are preferably rotated homogeneously with respect to one another. The angle by which the individual planes are rotated with respect to one another is preferably calculated to be $$\alpha = \frac{180}{z_o}$$

where $\alpha$ is the angle by which the planes are rotated with respect to one another and $z_o$ is the number of orifices per plane.

The diameter of the feed orifices through which the phosgene is added is preferably less than the separation of the planes in which the feed orifices are arranged. The diameter of the feed orifices, based on the diameter of the mixing chamber, is preferably in the range from 0.01 to 0.5, more preferably in the range from 0.02 to 0.3 and especially in the range from 0.03 to 0.25.

The feed orifices can open into the mixing chamber at any desired angle. The axes of the feed orifices preferably intersect with the axis of the mixing chamber; the feed orifices more preferably open into the mixing chamber at an angle of 90°.

The feed orifices through which the phosgene is added are preferably nozzle orifices. This means that the phosgene is fed to the mixing chamber through lines and a cross-sectional constriction in the form of a nozzle is formed at the end of the lines. The phosgene then exits from the nozzle into the mixing chamber. The feed orifice of the phosgene is preferably flush with the wall of the mixing chamber. The nozzles may have either circular orifices or orifices deviating from the circular shape.

The mixing chamber in which the amine is mixed with the phosgene is preferably rotationally symmetric. When the mixing chamber does not have a circular cross section, the diameter of the mixing chamber always means the hydraulic diameter.

At its downstream end, the mixing chamber preferably has a diameter constriction by virtue of which the reaction mixture is backmixed. The backmixing is effected as a result of the deflection of the flow owing to the diameter constriction.

The diameter constriction at the downstream end of the mixing chamber is preferably configured with an angle in the range from 10 to 80° relative to the axis of the mixing chamber. The diameter constriction at the downstream end is more preferably configured with an angle of from 15 to 60° and especially preferably with an angle of from 18 to 40° relative to the axis of the mixing chamber. The diameter constriction at the downstream end of the mixing chamber is preferably a conical constriction. The ratio of the diameter of the diameter constriction to which the cross section is reduced is, based on the diameter of the mixing chamber, in the range from 0.2 to 0.7, more preferably in the range from 0.25 to 0.65 and especially in the range from 0.3 to 0.6. As well as backmixing, the diameter constriction thus also results in acceleration of the reaction mixture.

For flow homogenization, the diameter constriction is preferably followed downstream by a zone with a constant diameter in which there is only minor backmixing.

The residence time of the reaction mixture in the zone with constant diameter is preferably not more than 50 ms, especially not more than 30 ms. The length of the zone with constant diameter based on the diameter of this zone (L/D ratio) is preferably in the range from 1 to 10, more preferably in the range from 1.5 to 9 and especially in the range from 2 to 8.

The zone with constant diameter is followed downstream by a zone with a cross-sectional enlargement, the cross-sectional enlargement having an opening angle based on the axis of the zone at which there is no discontinuity of flow. This means that the cross-sectional enlargement is configured in the form of a diffuser. The cross-sectional enlargement widens the diameter until the diameter of the reactor which is preferably configured as a tubular reactor is attained. In this context, it is possible that the diameter is widened stepwise, in which case a region with constant diameter is arranged between each of the individual stages in which the diameter is widened.

In order to prevent discontinuity of flow, the opening angle of the cross-sectional enlargement relative to the axis of the zone is preferably less than 15°, more preferably less than 10° and especially preferably less than 8°.

An example of the invention is shown in the drawing and is illustrated in detail in the description which follows.

The sole FIGURE shows an apparatus for mixing amine and phosgene in the liquid phase.

In processes for preparing isocyanates by reacting the corresponding amines with phosgene in the liquid phase, the amine is mixed with the phosgene, before the mixed reactants are fed to a reactor in which the reaction is effected.

An apparatus for mixing amine and phosgene comprises a mixing chamber 1 into which phosgene and amine are supplied. The amine is preferably added through an orifice 3 which is arranged coaxially to the mixing chamber 1. Alternatively, it is, however, also possible that the phosgene is supplied through the orifice 3 arranged coaxially to the mixing chamber. However, preference is given to adding the amine through the orifice 3 arranged coaxially to the mixing chamber. The orifice 3 arranged coaxially to the mixing chamber 1 is, for example, as shown here, configured in the form of a nozzle which projects into the mixing chamber 1.

In addition, the apparatus for mixing phosgene and amine comprises feed orifices 5 through which the phosgene or, in the case of addition of the phosgene through the orifice arranged coaxially to the axis of the mixing chamber, the amine is added. The feed orifices 5 are likewise preferably configured as nozzles. The feed orifices 5 are arranged in at least two planes 7, 9 which are arranged at right angles to the axis of the mixing chamber. The planes 7, 9 are shown here by dotted lines. In the embodiment shown here, the feed orifices 5 are arranged in two planes 7, 9. A first plane 7 is arranged downstream and a second plane 9 upstream of the orifice 3 arranged coaxially.

In addition to the embodiment shown here, with two planes 7, 9 in which the feed orifices 5 are arranged, it is alternatively also possible that the feed orifices are arranged in more than two planes. In the case that the feed orifices 5 are arranged in more than two planes 7, 9, in each case at least one plane is arranged upstream and at least one plane downstream of the orifice 3 arranged coaxially.

Preferably two feed orifices 5 are arranged in each plane 7, 9, in which case the feed orifices 5 each lie diametrically opposite one another. By virtue of the arrangement in which the feed orifices 5 are diametrically opposite one another, the main directions of the feed orifices 5 meet in the axis 11 of the mixing chamber 1.

The ratio of the distance $L_1$ of the first plane 7 from the orifice 3 arranged coaxially to the mixing chamber, based on the diameter $D_M$ of the mixing chamber 1, is preferably in the range from 0 to 1, more preferably in the range from 0.01 to 0.5 and especially in the range from 0.05 to 0.2. When feed orifices 5 are arranged in more than one plane downstream of the orifice 3 arranged coaxially to the mixing chamber, this distance is the distance of the plane which is the closest to the orifice 3 arranged coaxially to the mixing chamber.

The ratio of the distance $L_2$ of the second plane 9 which is arranged upstream of the orifice 3 which is arranged coaxially to the mixing chamber 1, based on the diameter $D_M$ of the mixing chamber 1, is likewise preferably in the range from 0 to 1, more preferably in the range from 0.01 to 0.5 and especially in the range from 0.05 to 0.2. When feed orifices 5 are arranged in more than two planes upstream of the orifice 3 arranged coaxially to the mixing chamber 1, this distance corresponds to the distance of the plane which is closest to the orifice 3.

At its downstream end, the mixing chamber 1 preferably has a diameter constriction 13. The diameter constriction 13 preferably has a conical configuration and is configured with an angle $\alpha$ in the range from 10 to 80°, preferably with an angle in the range from 15 to 60° and especially preferably with an angle of from 18 to 40° relative to the axis 11 of the mixing chamber 1.

The diameter constriction 13 is followed downstream by a zone of constant diameter 15. The zone 15 of constant diameter has a diameter $D_A$, where the ratio of the diameter $D_A$ of the zone 15 of constant diameter to the diameter $D_M$ of the mixing chamber 1, as already described above, is in the range from 0.2 to 0.7, more preferably in the range from 0.25 to 0.65 and especially in the range from 0.3 to 0.6. At the diameter constriction 13, the diameter decreases from the diameter $D_M$ of the mixing chamber 1 to the diameter $D_A$ of the zone 15 of constant diameter.

The zone 15 of constant diameter is followed downstream by a cross-sectional enlargement 17. The cross-sectional enlargement 17 is preferably configured in the form of a diffuser. The cross-sectional enlargement 17 has an opening angle β which is selected such that no discontinuity of flow occurs in the cross-sectional enlargement 17. Alternatively to the embodiment shown here with a conically widening cross-sectional enlargement 17, it is, for example, also possible that the diameter in the cross-sectional enlargement 17 widens stepwise. In this case, a region with constant diameter is arranged between each of the individual stages in which the diameter is widened. Alternatively, it is also possible that a region in which the diameter widens conically is formed between each of the individual stages.

The cross-sectional enlargement 17, however, more preferably has a conical configuration and the opening angle β of the cross-sectional enlargement 17 is preferably <15°, more preferably <10° and especially preferably <8°.

The length of the cross-sectional enlargement 17 is selected such that the diameter widens to the diameter of the reactor which follows downstream of the apparatus for mixing the amine and phosgene, which is not shown here.

In order to achieve a short residence time and high mixing speeds in the mixing chamber 1, the ratio of the length $L_M$ of the mixing chamber 1 based on the diameter $D_M$ is preferably in the range between 1 and 2 and especially in the range from 1 to 1.5. The ratio of the length $L_A$ of the zone 15 of constant diameter based on the diameter $D_A$ of the zone of constant diameter is preferably in the range from 1 to 10, more preferably in the range from 1.5 to 9 and especially in the range from 2 to 8.

EXAMPLE

To prepare MDI/PMDI, an apparatus which comprises a mixing chamber having a diameter of 40 mm and a length of 66 mm is used. A feed unit for the amine opens into the mixing chamber and projects 26 mm into the mixing chamber, with a diameter of 20 mm and a nozzle diameter of 5.5 mm. For the supply of the phosgene, two feed orifices are arranged diametrically 6 mm above the exit cross section of the central nozzle, and two feed orifices diametrically 6 mm below the exit cross section of the central nozzle. The diameter of the feed orifices above the exit cross section of the central nozzle is 5.1 mm with a diameter of the feed unit of 15 mm, and the nozzle diameter of the feed orifices below, i.e. downstream of the orifice of the central nozzle, is 6.9 mm with a diameter of the feed unit of 20 mm.

The mixing chamber has a conical constriction with an angle of 25°, the diameter decreasing from the mixing chamber diameter of 40 mm to the exit diameter of 25 mm. The total length of the mixing chamber comprising the cylindrical part and the conical part is 66 mm. The mixing chamber is followed downstream by a zone of constant diameter with a length of 180 mm. The zone of constant diameter is followed downstream by an enlargement with an opening angle of 6°. At the enlargement, the diameter increases to the diameter of the downstream tubular reactor.

The central nozzle is used to feed in 3.75 m³/h of an amine-containing stream, and the feed orifices to feed in 11.2 m³/h of a phosgene-containing stream. The amine-containing stream comprises from 34 to 36% by weight of MDA/PMDA with a proportion of from 50.4 to 51.1% by weight of MDA and from 54 to 56% by weight of monochlorobenzene, and the phosgene-containing stream comprises from 66 to 70% by weight of phosgene and from 30 to 34% by weight of monochlorobenzene.

The residence time in the mixing zone is 17 ms. The residence time in the zone with constant diameter is about 21 ms.

| List of reference numerals | |
|---|---|
| 1 | mixing chamber |
| 3 | orifice coaxial to the mixing chamber |
| 5 | feed orifice |
| 7 | first plane |
| 9 | second plane |
| 11 | axis |
| 13 | diameter constriction |
| 15 | zone of constant diameter |
| 17 | cross-sectional enlargement |
| $D_A$ | diameter of zone 15 of constant diameter |
| $D_M$ | diameter of mixing chamber 1 |
| $L_A$ | length of zone 15 of constant diameter |
| $L_M$ | length of mixing chamber 1 |
| $L_1$ | distance of first plane 7 from orifice 3 |
| $L_2$ | distance of second plane 9 from orifice 3 |
| α | angle at which the diameter constriction 13 is configured |
| β | opening angle of the cross-sectional enlargement 17 |

The invention claimed is:

1. A process for preparing isocyanates, the process comprising reacting at least one amine with a phosgene in a liquid phase, optionally in the presence of at least one inert medium, to form an isocyanate,
wherein:
the at least one amine and the phosgene are first mixed in a mixing chamber to produce a reaction mixture which is then fed to a reactor;
the at least one amine is added through a coaxial orifice arranged coaxially to the mixing chamber and the phosgene is added through a first feed orifice and a second feed orifice situated in at least a first plane and a second plane, respectively, arranged at right angles to the axis of the mixing chamber, or
the phosgene is added through the coaxial orifice arranged coaxially to the mixing chamber and the at least one amine is added through the first feed orifice and the second feed orifice situated in at least the first plane and the second plane, respectively, arranged at right angles to the axis of the mixing chamber;
the first plane is arranged in an upstream of the coaxial orifice and the second plane is arranged in a downstream of the coaxial orifice;
the mixing chamber comprises a diameter constriction at a downstream end thereof, such that the reaction mixture is backmixed by the diameter constriction;
the diameter constriction at the downstream end of the mixing chamber is configured with an angle (α) ranging from 10 to 80° relative to the axis of the mixing chamber; and
a mean residence time of the reaction mixture in the mixing chamber is not more than 18.5 ms.

2. The process according to claim 1, wherein the phosgene is added through at least the first feed orifice and the second feed orifice.

3. The process according to claim 2, wherein the feed orifices through which the phosgene is added are arranged such that a longitudinal axis of the first feed orifice and a longitudinal axis of the second feed orifice meet with the axis of the mixing chamber.

4. The process according to claim 1, wherein the diameter constriction at the downstream end of the mixing chamber is configured with an angle ($\alpha$) ranging from 18 to 40° relative to the axis of the mixing chamber.

5. The process according to claim 1, wherein a first zone having a constant diameter in which only minor backmixing occurs is situated in a downstream of the mixing chamber.

6. The process according to claim 5, wherein the residence time of the reaction mixture in the first zone having the constant diameter is not more than 50 ms.

7. The process according to claim 5, wherein a second zone having a cross-sectional enlargement is situated in a downstream of the first zone, such that the cross-sectional enlargement has an opening angle ($\beta$) at which has no discontinuity of flow occurs.

8. The process according to claim 7, wherein the opening angle ($\beta$) of the cross-sectional enlargement relative to the axis of the second zone is less than 15°.

9. The process of claim 1, wherein the at least one amine is added through the coaxial orifice and the phosgene is added through the first feed orifice and the second feed orifice.

10. The process of claim 1, wherein a ratio of a diameter of the coaxial orifice to a diameter of the mixing chamber ranges from 0.05 to 0.5.

11. The process of claim 1, wherein a ratio of a distance $L_1$ of the first plane from the coaxial orifice to a diameter $D_m$ of the mixing chamber ranges from 0 to 1, and a ratio of a distance $L_2$ of the second plane from the coaxial orifice to the diameter $D_m$ of the mixing chamber ranges from 0 to 1.

12. The process of claim 1, wherein a ratio of a length $L_m$ of the mixture chamber to a diameter $D_m$ of the mixing chamber ranges from 1 to 2.

13. The process of claim 5, wherein a ratio of the length $L_A$ of the first zone to a diameter $D_A$ of the first zone ranges from 1 to 10.

* * * * *